US012758421B2

(12) United States Patent
Takakuwa et al.

(10) Patent No.: US 12,758,421 B2
(45) Date of Patent: Oct. 13, 2026

(54) HEATER

(71) Applicant: Kao Corporation, Tokyo (JP)

(72) Inventors: Hotaka Takakuwa, Sumida-ku (JP); Masaki Hiwatashi, Utsunomiya (JP)

(73) Assignee: Kao Corporation, Tokyo (JP)

( * ) Notice: Subject to any disclaimer, the term of this patent is extended or adjusted under 35 U.S.C. 154(b) by 243 days.

(21) Appl. No.: 18/559,611

(22) PCT Filed: Feb. 14, 2022

(86) PCT No.: PCT/JP2022/005681

§ 371 (c)(1),
(2) Date: Nov. 8, 2023

(87) PCT Pub. No.: WO2022/249577

PCT Pub. Date: Dec. 1, 2022

(65) Prior Publication Data

US 2024/0238119 A1 Jul. 18, 2024

(51) Int. Cl.

*A61F 7/03* (2006.01)
*A61F 7/00* (2006.01)
*A61F 7/02* (2006.01)

(52) U.S. Cl.

CPC ...... *A61F 7/034* (2013.01); *A61F 2007/0004* (2013.01); *A61F 2007/0062* (2013.01);
(Continued)

(58) Field of Classification Search

CPC .. A61F 7/034; A61F 7/032; A61F 7/03; A61F 2017/0004; A61F 2017/0062;
(Continued)

(56) References Cited

U.S. PATENT DOCUMENTS

2004/0035410 A1 2/2004 Igaki et al.
2010/0198325 A1 8/2010 Ishikawa
2019/0216639 A1 7/2019 Bruder

FOREIGN PATENT DOCUMENTS

CN 110958865 A 4/2020
CN 112118814 A 12/2020
(Continued)

OTHER PUBLICATIONS

Translation of CN11218814 (Year: 2020).*
(Continued)

*Primary Examiner* — Beverly M Flanagan
(74) *Attorney, Agent, or Firm* — Oblon, McClelland, Maier & Neustadt, L.L.P.

(57) ABSTRACT

A warming device containing a topsheet to be located close to a skin of a user, a backsheet to be located far from the skin of the user, and a heat generating element interposed between the topsheet and the backsheet. The heat generating element contains an oxidizable metal, a carbon material, an electrolyte, and water, the heat generating element is configured to generate vapor from the heat generating element itself as heat is generated, the topsheet includes a breathable fiber sheet including fibers containing at least a polyethylene terephthalate resin, and the topsheet contains first fibers having a fiber diameter of more than 15 μm in plan view as measured by observation under a scanning electron microscope.

12 Claims, 4 Drawing Sheets

(52) U.S. Cl.
CPC ................. *A61F 2007/0222* (2013.01); *A61F 2007/0258* (2013.01)

(58) Field of Classification Search
CPC ...... A61F 2017/0222; A61F 2017/0203; A61F 2017/0225; A61F 2017/0244; A61F 2017/0052; A61F 2017/0088; A61F 2017/036
USPC .......................................................... 607/108
See application file for complete search history.

(56) References Cited

FOREIGN PATENT DOCUMENTS

| | | | |
|---|---|---|---|
| EP | 3 597 808 | A1 | 1/2020 |
| JP | 11-165767 | A | 6/1999 |
| JP | 3901660 | B2 | 4/2007 |
| JP | 2009-225975 | A | 10/2009 |
| JP | 2015-123336 | A | 7/2015 |
| TW | 202033169 | A | 9/2020 |
| WO | WO 2018/167881 | A1 | 9/2018 |
| WO | WO 2020/105529 | A1 | 5/2020 |

OTHER PUBLICATIONS

Extended European Search Report issued May 9, 2025 in European Patent Application No. 22810861,9, 10 pages.
International Search Report issued Mar. 22, 2022 in PCT/JP2022/005681 filed on Feb. 14, 2022, 2 pages.

* cited by examiner

HEATER

CROSS REFERENCE TO RELATED APPLICATIONS

This application is a National Stage entry under 35 U.S.C. § 371 of PCT/JP2022/005681, filed on Feb. 14, 2022, and claims priority to PCT/JP2021/019634, filed on May 24, 2021. The entire contents of both are incorporated herein by reference.

TECHNICAL FIELD

The present invention relates to a warming device.

BACKGROUND ART

The present applicants have proposed an eye-use water-vapor-generating heating sheet capable of supplying warm water vapor to the eyes and around the eyes (see Patent Literature 1). The eye-use vapor-generating heating sheet includes, on the skin side of a wearer, a first moisture-permeable sheet and a second moisture-permeable sheet, and a water vapor generation composition is successively covered with the first moisture-permeable sheet and the second moisture-permeable sheet.

CITATION LIST

Patent Literatures

Patent Literature 1: US 2004/035410 A1

SUMMARY OF INVENTION

The present invention relates to a warming device.

The warming device includes a topsheet to be located close to the skin of a user, a backsheet to be located far from the skin of the user, and a heat generating element interposed between the topsheet and the backsheet.

The heat generating element preferably contains an oxidizable metal, a carbon material, an electrolyte, and water.

The heat generating element is preferably configured to generate vapor from the heat generating element itself as heat is generated.

The topsheet preferably has a skin-facing surface that includes a breathable fiber sheet including fibers containing at least a polyethylene terephthalate resin.

The topsheet preferably includes first fibers having a fiber diameter of more than 15 μm in plan view as measured by observation under a scanning electron microscope.

DESCRIPTION OF EMBODIMENTS

The warming device disclosed in Patent Literature 1 is typically packed in a package in a compressed state, and thus sheet materials included in the warming device are compressed. There is therefore room for improvement in the recovery of bulk manifested immediately after production of the sheet materials. Accordingly, there is also room for improvement in fitting properties and feeling of use during use of the warming device due to the bulk of the sheet materials.

The present invention therefore relates to a warming device having good bulk recovery after opening and having high fitting properties and feeling of use immediately after use.

The present invention will now be described on the basis of preferred embodiments thereof with reference to drawings. A warming device of the present invention is brought into contact with a heating object and provides heat to the heating object when used.

Figure 1:
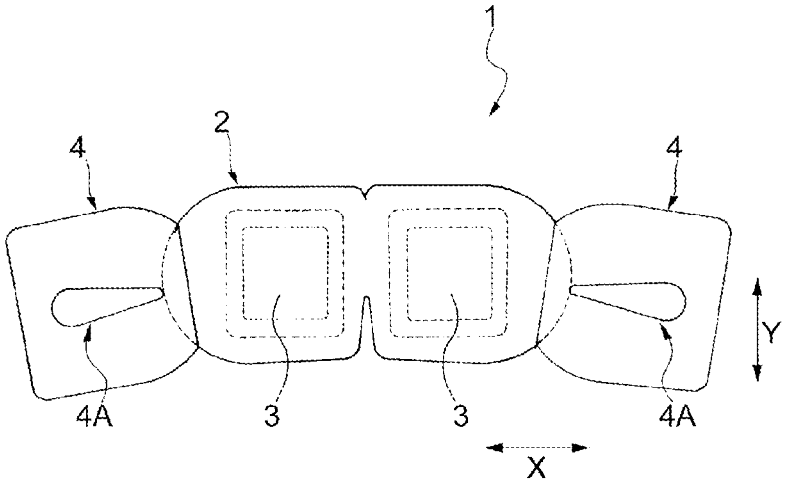
FIG. 1 is a plan view showing an embodiment of a warming device of the present invention.

FIG. 1 shows an embodiment of the warming device of the present invention. The warming device 1 shown in the figure is what is called an eye mask type. When used, the warming device is brought into contact with eyes of a human so as to cover the eyes as a heating object and provides heat to the eyes and around the eyes.

The warming device 1 is configured to generate water vapor heated at a predetermined temperature, and accordingly heat can be provided to a heating object. In the following description, the skin or the eyes of a user are exemplified as the heating object unless otherwise noted.

As shown in FIG. 1, the warming device 1 includes a main body 2 having a shape that is so long in the lateral direction X as to cover the eyes of a user when used, heat generating elements 3 held in the main body 2, and a pair of ear loop portions 4, 4.

The ear loop portions 4 are provided in the respective outer edge regions in the lateral direction X of the main body 2 and are reversible outward in the lateral direction X. Accordingly, the ear loop portions 4, 4 can be hung on the respective ears of a user to maintain the main body 2 that covers the eyes of the user.

From the viewpoint of improvement in wearing comfort, the sheet material included in the ear loop portion 4 is preferably an elastic sheet. In the following description, the direction corresponding to the longitudinal direction of the warming device 1 is also called a lateral direction X, and the direction orthogonal to the lateral direction X is also called a vertical direction Y.

Figure 2:
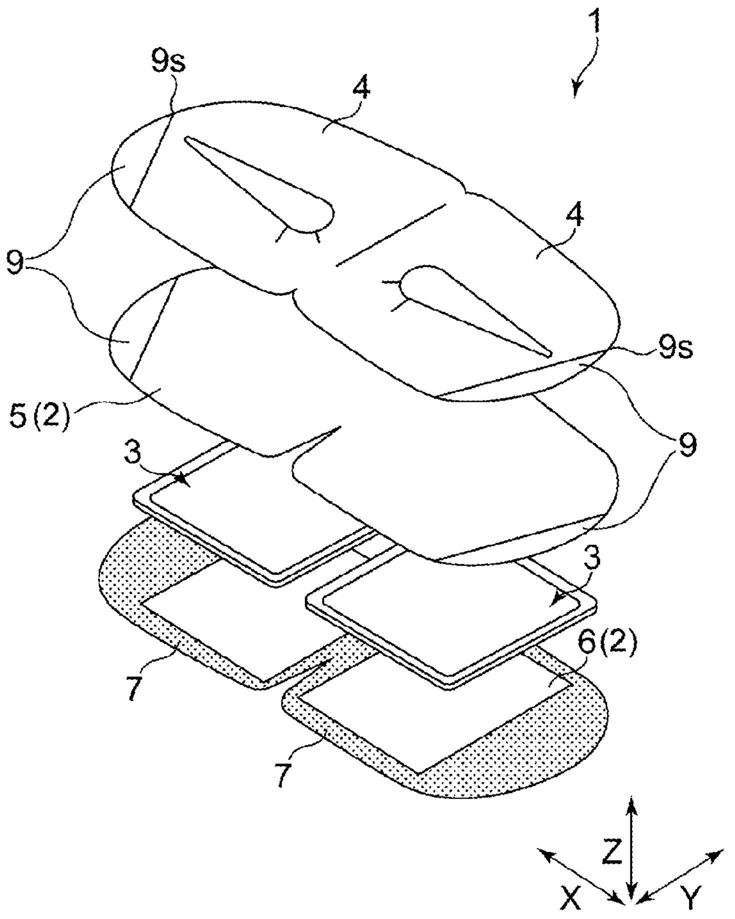
FIG. 2 is an exploded perspective view of the warming device shown in FIG. 1.
Figure 3:
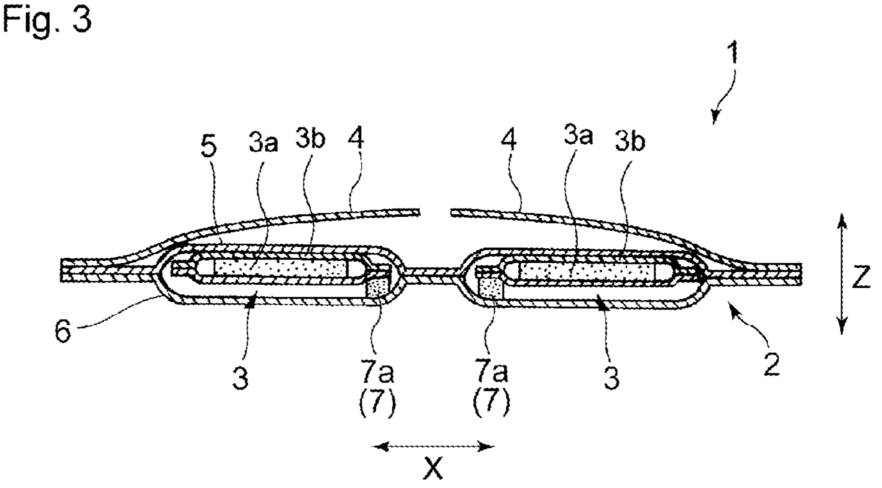
FIG. 3 is a sectional view along a lateral direction as the longitudinal direction of the warming device shown in FIG. 1.

FIG. 2 shows an exploded perspective view of the warming device 1. FIG. 3 shows a sectional view along the lateral direction X (longitudinal direction) of the warming device 1. The main body 2 of the warming device 1 shown in the figures is long in one direction.

The main body 2 includes a topsheet 5 to be located close to the skin of a user and a backsheet 6 to be located far from the skin of a user and has a flattened shape.

The topsheet 5 preferably constitutes a face to come into contact with a heating object such as the eyes of a human when the warming device 1 is used.

The backsheet 6 is a face to be far from the skin of a user and constitutes the outer surface of the warming device 1. In other words, in FIG. 2 and FIG. 3, the upper side is close to the skin of a user, whereas the lower side in the figures is far from the skin of a user.

The topsheet 5 and the backsheet 6 shown in FIG. 2 and FIG. 3 are laminated and joined together through an adhesive 7 such as a hot melt adhesive, and accordingly, two heat generating elements 3, 3 are interposed between the sheets 5, 6 while separated from each other in the lateral direction X.

Of the topsheet 5 and the backsheet 6, at least the surface (hereinafter also called a "skin-facing surface") of the topsheet 5 to face a heating object such as the skin preferably includes a fiber sheet having breathability, and more preferably, the whole topsheet 5 includes the fiber sheet. The topsheet 5 and the backsheet 6 may each independently have a single layer structure or a multiple layer structure.

Each of the sheets 5, 6 will be described later in detail. The fiber sheet is a constituent fiber aggregate in which a plurality of constituent fibers are maintained in a sheet shape by at least one of entanglement, fusion, and joining.

The heat generating element 3 interposed between the topsheet 5 and the backsheet 6 in the main body 2 is configured to generate water vapor heated at a predetermined temperature as heat is generated by reaction with oxygen in air to generate heat. In other words, the heat generating element 3 in the disclosure generates vapor from the heat generating element 3 itself as heat is generated.

Specifically, the heat generating element 3 includes a heat generating portion 3*a* containing an oxidizable metal that undergoes oxidation reaction with oxygen in air to generate heat, a carbon material such as activated carbon that catalyzes the oxidation reaction, an electrolyte, and water. Each of the oxidizable metal and the carbon material is preferably a powder.

As the heat generating portion 3*a*, for example, a heat generating sheet including a fiber sheet further containing a fiber material in addition to the oxidizable metal, the carbon material, the electrolyte, and the water or a portion including a layer of a paste-like or powdery heat generating composition containing the oxidizable metal, the carbon material, the electrolyte, and the water can be used.

From the viewpoint of sufficiently retaining water that can increase the generation amount of water vapor by heat from the heat generating element 3, the heat generating element 3 preferably further includes a humectant layer containing a humectant such as a water absorbing polymer adjacent to the heat generating portion 3*a*. Alternatively, a humectant is preferably mixed in the heat generating sheet or the heat generating composition.

The heat generating sheet and the heat generating composition may be used singly, or at least one of the heat generating sheet and the heat generating composition stored in a bag prepared by laminating a plurality of sheet materials may be used. As materials included in the heat generating sheet or the heat generating composition, for example, materials disclosed in JP 2003-102761 A or JP 2006-340928 A may be used.

The sectional view shown in FIG. 3 shows the fixed state of a flattened heat generating element 3 in which a heat generating portion 3*a* is stored in a bag 3*b*. In the heat generating element 3 shown in the figure, the outer surface of the bag 3*b* and the inner surface of the backsheet 6 of the warming device 1 are fixed through an adhesive fixed portion 7*a*, 7*a* formed from an adhesive 7, and the other surface is not fixed to the backsheet 6. Each of the adhesive fixed portions 7*a*, 7*a* is located in the center region in the lateral direction X of the warming device 1 and extends in the vertical direction Y of the warming device 1. With such a structure, the heat generating element 3 with high softness is placed to come into close contact with a heating object such as the eyes of a user and the vicinity thereof when the warming device 1 is used, and accordingly, heat can be efficiency provided to the heating object.

In FIG. 2, the ear loop portions 4 shown in the figure are made from a sheet material, and in the sheet material, insertion portions 4A extending in the lateral direction X are formed. The insertion portions 4A are holes through which the ears are inserted when the ear loop portions 4 are put on the ears. Alternatively, the insertion portions 4A may be penetration slits or the like thorough which the ears can be inserted.

Figure 4:
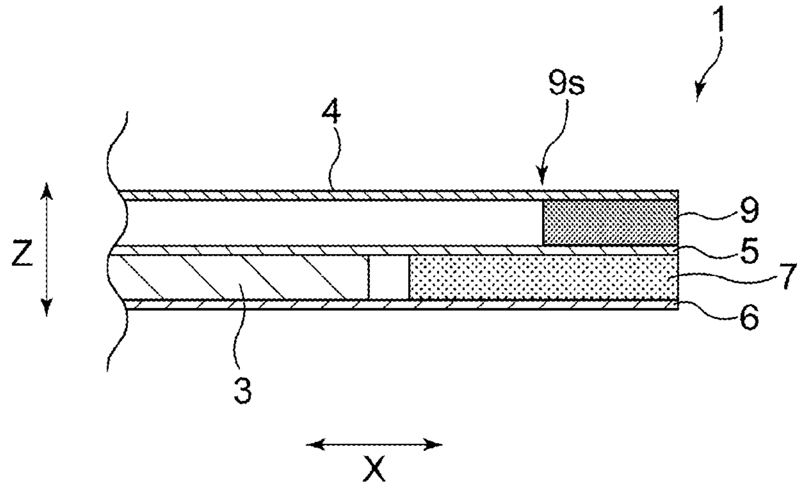
FIG. 4 is an enlarged sectional view of the warming device shown in FIG. 3.

As shown in FIG. 2 and FIG. 4, the ear loop portions 4 are joined in the respective outer edge regions in the lateral direction X to the outer surface of the topsheet 5 in the main body 2, and accordingly, joint regions 9 in which the main body 2 is joined to the ear loop portions 4 are formed. The joint region 9 also functions as a bending portion when the ear loop portion 4 is reversed around a joint edge 9*s* as the axis.

FIG. 4 is a sectional view showing an example arrangement of the heat generating element 3, the topsheet 5, the backsheet 6, and the joint region 9. The joint region 9 between the main body 2 and the ear loop portion 4 shown in FIG. 2 and FIG. 4 is continuously joined from the joint edge 9*s* as the inner edge in the lateral direction X of the joint region 9 to the outer edge in the lateral direction X of the main body 2 and has a semi-elliptical shape.

As shown in FIG. 4, the joint region 9 is formed by joining the topsheet 5 and the ear loop portion 4. The joint region 9 also functions as a bending portion when the ear loop portion 4 is reversed around the joint edge 9*s* as the axis. The joint region 9 shown in FIG. 2 and FIG. 4 are formed by continuous joining. Alternatively, the joint region may be formed by intermittent joining.

In the warming device 1 having the above structure, the topsheet 5 to come into contact with a heating object when the warming device is used preferably includes fibers having a predetermined structure. In the following description, a breathable fiber sheet as a preferred embodiment of the topsheet 5 will be described.

Specifically, in the topsheet 5, fibers included in the sheet preferably contain at least a polyethylene terephthalate (PET) resin. In other words, the topsheet 5 is an aggregate of fibers containing at least a PET resin as a type of the constituent fibers.

The fibers containing at least a PET resin are likely to have a higher rigidity than fibers containing other thermoplastic resins. When a warming device 1 that includes a topsheet 5 including the fibers containing at least a PET resin is even compressed in the thickness direction in a step before use, such as packaging and distribution, and the packing bag is opened to release the compressed state, the bulk of the topsheet 5 is easily and rapidly recovered, and high softness, high fitting properties, and high feeling of use are achieved immediately after use.

The topsheet 5 contains first fibers having a predetermined fiber diameter. Specifically, the fiber diameter of the first fibers contained in the topsheet 5 is preferably more than 15 μm, more preferably 20 μm or more, and even more preferably 25 μm or more and is preferably 60 μm or less, more preferably 50 μm or less, even more preferably 45 μm or less, and further preferably 40 μm or less. In another embodiment, the fiber diameter can be furthermore preferably 30 μm or less.

Even when a warming device including first fibers having such a fiber diameter is, for example, stored in a packing bag to be compressed in the thickness direction, the bulk of the topsheet included in the warming device is recovered immediately after compression release by, for example, taking out from the packing bag, and the fitting properties is improved when the warming device is used.

The above "constituent fibers containing at least a PET resin" may be just first fibers having the above fiber diameter, may be additional fibers other than the first fibers included in the topsheet, or may be all fibers of the first fibers and additional fibers included in the topsheet. From the viewpoint of improvement in softness, fitting properties, and feeling of use, at least the first fibers preferably contain a PET resin. In this case, the content of the PET resin contained in the first fibers is preferably 20% by mass or more, more preferably 40% by mass or more, even more preferably 70% by mass or more, and further preferably 100% by mass.

The fiber diameter of first fibers contained in a topsheet 5 can be determined by observing the topsheet in plan view under a scanning electron microscope (SEM), for example, in the following manner. The determination method of the fiber diameter will be applied as the common method for determining the fiber diameter of any fibers described in the present description.

First, whether a topsheet contains fibers having a single fiber diameter or contains fibers having a plurality of fiber diameters is determined by preparing a histogram of the frequency of the number of fibers and the distribution of fiber diameters (hereinafter also simply called a "histogram").

Specifically, a measurement sample of a topsheet to be determined is prepared by spraying cold spray on a warming device to solidify an adhesive and carefully releasing the topsheet or directly cutting out the topsheet of a warming device, for example. The measurement sample measures 2 cm×2 cm. In the preparation, the measurement sample is prepared such that the skin-facing surface can be differentiated from the surface to be placed far from the skin of a user (hereinafter also called a "non-skin-facing surface") by any method. The above extraction method of a measurement sample from a topsheet is common to other methods in the disclosure.

Next, from the measurement sample, fiber diameters and the number of fibers are determined, and a histogram is prepared. The fiber diameters and the number of fibers are determined on one surface of a measurement sample as follows: the sample is subjected to SEM observation in plan view; fibers are observed, for example, at a magnification of 2,000×; and a two-dimensional image is prepared to determine the fiber diameters and the number of fibers. For the number of fibers, a continuous fiber in a prepared two-dimensional image is counted as one. The observation is repeated until the number of fibers reaches 100 or more while the SEM observation region is changed. The observation may also be performed by using an image analysis software. For example, Photoshop (manufactured by Adobe) can be used as the image analysis software.

The fiber diameter is the maximum diameter of lines orthogonal to the longitudinal direction of a fiber except defects such as fiber aggregates, fiber intersections, and polymer droplets.

The above measurement is performed on the skin-facing surface of a measurement sample; the range of a fiber diameter class for preparing a histogram is selected from a range of 0.1 to 0.5 μm; and from the measurement result, a histogram of the frequency of the number of fibers and the distribution of fiber diameters is prepared.

When a prepared histogram has only one fiber diameter distribution peak, the measurement surface side of a topsheet is determined to include only one type of fibers. Alternatively, when a prepared histogram has two or more fiber diameter distribution peaks, the measurement surface side of a topsheet is determined to include multiple types of fibers. A peak is a fiber diameter position with the vertex at which the frequency of the number of fibers turns from positive to negative.

Whether a topsheet includes a single fiber layer or a plurality of fiber layers can be determined as follows: for example, a cross section of a measurement sample is observed under a microscope, an SEM, or the like to identify the presence of fiber layers or the boundary thereof on the basis of differences in fiber diameters or fiber structures; or fibers are stained.

When it is difficult to visually determine whether a plurality of fiber layers are included, a histogram is prepared also for the other surface (non-skin-facing surface) of a measurement sample, and the pattern of the histogram for one surface (skin-facing surface) of the measurement sample is compared with the pattern of the histogram for the other surface. When these histograms are different in the number of peaks or the peak position, a plurality of fiber layers are determined to be included. In contrast, when these histograms have the same number of peaks or the same peak positions, a single fiber layer is determined to be included.

The above method is performed to determine whether a topsheet contains only the first fibers or further contains other fibers in addition to the first fibers. When only one peak is observed in a fiber diameter distribution, the fiber diameter at the peak in the histogram is regarded as the fiber diameter of the first fibers. When two or more peaks are observed in a fiber diameter distribution, the fiber diameter at the peak located at the largest fiber diameter side of the peaks in the fiber diameter distribution is regarded as the fiber diameter of the first fibers.

A typical warming device using heat generated by oxidation reaction of iron is stored in a packing bag that blocks outside air from entering while compressed in the absence of oxygen before use of the warming device such that contact with oxygen is blocked to prevent iron from undergoing unintended oxidation reaction. In this case, even when a topsheet is produced such that the topsheet can manifest softness or fitting properties, the sheet is likely to be compressed in the thickness direction at the time of packing or after packing a warming device including the topsheet in a packing bag or during distribution of the warming device packed in a packing bag, and the softness or the fitting properties due to the topsheet may be difficult to be manifested as designed. There is therefore room for improvement.

According to the present embodiment, fibers having a predetermined fiber diameter and containing a PET resin are used as the constituent fibers in the topsheet 5. Accordingly, the high rigidity of the PET manifests compression resistance, and when a packing bag containing a sheet that have been compressed in the sheet thickness direction in a step before use, such as packing and distribution, is opened to release the compressed state, the bulk of the topsheet is easily recovered. Consequently, high fitting properties and feeling of use are manifested immediately after use, and good texture is achieved.

In addition, heat during use, generation of water vapor, and hot air by heat allow fibers included in the topsheet 5 to have larger distances between the fibers, and this efficiently makes the sheet bulky. As a result, over a long time from the start of use to the end of use of the warming device 1, the softness and the fitting properties are manifested at high levels.

From the viewpoint of achieving rapid recovery of the bulk of the topsheet 5 as well as the softness, the fitting properties, and the feeling of use at the time of use and of preventing fiber fuzz to improve the texture on the surface to come into contact with the skin, the topsheet 5 preferably contains, in addition to the above first fibers, at least one type of fibers different in fiber type from the first fibers.

The fibers in the topsheet 5 are present in the following states, for example. Specific examples include (i) a state in which in a portion to come into contact with a heating object such as the skin, the first fibers and additional fibers other than the first fibers are uniformly mixed; (ii) a state in which in a plan view of a portion to come into contact with a heating object such as the skin, the portion includes a portion including only the first fibers and a portion including only additional fibers other than the first fibers; and (iii) a state in which the topsheet 5 has a multiple layer structure including two or more fiber layers, and only one fiber layer includes the first fibers.

Of them, from the viewpoint of preventing fiber fuzz to further improve the sheet texture and of manifesting the softness and the fitting properties more effectively, the topsheet 5 is preferably in the state (iii).

From a similar viewpoint, in the fiber sheet included in the topsheet, the sheet form is preferably maintained by at least one of fusion and entanglement of constituent fibers such that the fibers are in contact with each other to have contact parts.

In particular, the above sheet form preferably includes a nonwoven fabric. Examples of the nonwoven fabric in which fibers are entangled include a spunlace nonwoven fabric, an air-through nonwoven fabric, a needle punching nonwoven fabric, a chemically bonded nonwoven fabric, and a thermally bonded nonwoven fabric. In an example method of making a sheet in the state (iii), two or more fiber webs or nonwoven fabrics are entangled or fused. For example, in an air-through nonwoven fabric, the above contact part includes a part in which constituent fibers are simply in contact with each other and entangled as well as a part in which fibers are partly fused to each other. Hence, the constituent fibers are easily fixed, and constituent fiber fuzz or fall is advantageously suppressed.

In addition, the nonwoven fabric or the constituent fibers thereof may be subjected to surface treatment with a silicone, a surfactant, or the like, and the treated product may be used.

In addition to the above nonwoven fabric, for example, a foam sheet prepared from a thermoplastic resin such as polyethylene and polyurethane may be used. Such a sheet material may manifest intended characteristics by mixing multiple types of fibers different in fiber material, fiber diameter, fiber crimping degree, or the like or by combining a plurality of sheet materials.

Figure 5:
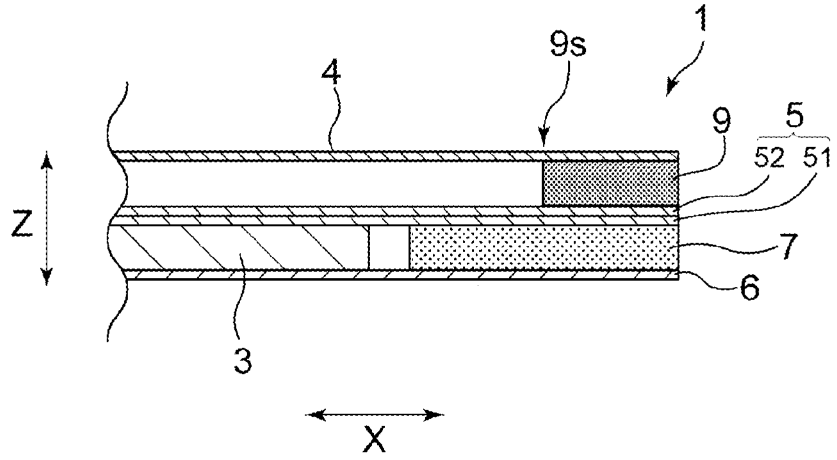
FIG. 5 is an enlarged sectional view along the lateral direction of another embodiment of the warming device.

As a preferred embodiment of the topsheet 5, a topsheet 5 having a multiple layer structure including two or more fiber layers preferably has at least a first fiber layer 51 including the first fibers and a second fiber layer 52 including, as additional fibers other than the first fibers, fibers different in fiber diameter from the first fibers, as shown in FIG. 5. Specifically, as in the embodiment, the topsheet preferably has a second fiber layer 52 including second fibers as the fibers having a smaller fiber diameter than the first fibers.

In addition, the first fiber layer 51 preferably includes no second fibers, and the second fiber layer 52 preferably includes no first fibers. In other words, the topsheet 5 preferably has at least a fiber layer including the first fibers and a fiber layer including fibers other than the first fibers.

As described above, by providing a plurality of fiber layers including fibers having different fiber diameters, the warming device can have such intended functions in the respective fiber layers as to manifest the recovery function of sheet bulkiness in a fiber layer including the first fibers and to manifest good texture or feel of the topsheet in a fiber layer including the second fibers. As a result, the topsheet 5 can be configured to manifest the above multiple functions efficiently and simultaneously, and such a topsheet can be further efficiently produced.

For convenience of explanation, in the following description, an embodiment of the topsheet 5 (see FIG. 5) having a two-layer structure in which the first fiber layer 51 is adjacent to the second fiber layer 52 shown in FIG. 5 will be described as an example, but the number or fiber layers is not specifically limited as long as the effect of the invention is achieved. For example, in an illustrative embodiment (example 1), a first fiber layer 51 may be provided to be adjacent to a second fiber layer 52, and on the outer surface of at least one of the first fiber layer 51 and the second fiber layer, one or more additional fiber layers may be provided. Alternatively, in another illustrative embodiment (example 2), between a first fiber layer 51 and a second fiber layer 52, one or more additional fiber layers may be further provided.

The fibers included in fiber layers provided to be adjacent to each other preferably include fibers having different fiber diameters. In other words, in the case of example 1, when a third fiber layer is provided on the outer surface of the first fiber layer 51, the fiber diameter in the third fiber layer may be the same as the fiber diameter in the second fiber layer or may be different from the fiber diameter in the first fiber layer and from the fiber diameter in the second fiber layer.

For convenience of explanation, in the topsheet 5 shown in FIG. 5, the boundary between the fiber layers included in the topsheet 5 is clear, but the topsheet is not limited to the embodiment. In other words, in a topsheet having a multiple layer structure, the boundary between fiber layers may be clear, or the boundary between fiber layers may be unclear.

In each case, when the topsheet 5 is viewed along the thickness direction, the content of constituent fibers in the fiber layers is preferably changed step-by-step, continuously, or a combination thereof from the viewpoint of handling properties of the topsheet during production or use.

In the disclosure, "including no fibers" means that the fibers are not intentionally included in a fiber layer and includes both the case in which the fibers are not included in a fiber layer at all and the case in which the fibers are inevitably included in a fiber layer. Examples of the latter case include a case in which other unintended fibers are inevitably mixed where first fibers included in a first fiber layer 51 cross the boundary between fiber layers and unintentionally enter a second fiber layer.

When the topsheet 5 has at least the first fiber layer 51 and the second fiber layer 52, the fiber diameter of second fibers included in the second fiber layer 52 is preferably 6 μm or more, more preferably 10 μm or more, and even more preferably 13 μm or more and is preferably 30 μm or less, more preferably 25 μm or less, even more preferably 20 μm or less, and further preferably 17 μm or less.

The second fibers preferably have a smaller fiber diameter than the fiber diameter of the first fibers.

By using second fibers having such a fiber diameter, the fiber rigidity is reduced, and good texture or smooth feel can be achieved when the topsheet comes into contact with the skin.

The fiber diameter of the second fibers can be determined by substantially the same measurement method as for the fiber diameter of the first fibers while the topsheet is observed in plan view under a scanning electron microscope.

In a topsheet 5 having at least the first fiber layer 51 and the second fiber layer 52, as for the arrangement, the first fiber layer 51 is preferably provided at the side far from the skin of a user as shown in FIG. 5 when the warming device is used. As shown in the figure, the second fiber layer 52 is also preferably provided on a skin-contact surface that is in direct contact with the skin of a user when the warming device is used.

In other words, the second fiber layer 52 preferably constitutes the skin-facing surface and is preferably provided to come into contact with the skin of a user.

The first fiber layer 51 is preferably provided so as not to come into contact with the skin of a user. In an embodiment shown in FIG. 5, the first fiber layer 51 constitutes the non-skin-facing surface of the topsheet 5, is provided at the closest side to the heat generating element 3, and is provided to be adjacent to the heat generating element 3.

The above arrangement of the fiber layers can prevent the first fibers having a relatively high rigidity due to a contained PET resin from coming into direct contact with the skin of a user, and thus a user can sense softness and smooth feel of the topsheet.

When the topsheet 5 has the first fiber layer 51, the first fiber layer 51 preferably further includes, in addition to the first fibers, third fibers having a smaller fiber diameter than the first fibers and having a larger fiber diameter than the second fibers. In other words, the first fiber layer 51 preferably includes multiple types of fibers including at least the first fibers and the third fibers and more preferably includes only the first fibers and the third fibers but preferably includes no second fibers except inevitably mixed fibers.

By adding, to the first fiber layer 51, the third fibers satisfying such a predetermined relation of fiber diameter, the topsheet can have higher softness, and the fitting properties are further improved when the warming device is used, as compared with the structure including only the first fibers with high rigidity.

When the first fiber layer 51 further includes the third fibers, the fiber diameter of the third fibers is preferably 15 μm or more, more preferably 18 μm or more, and even more preferably 20 μm or more and is preferably 50 μm or less, more preferably 40 μm or less, even more preferably 30 μm or less, and further preferably 24 μm or less, provided that the fiber diameter of the third fibers is smaller than the fiber diameter of the first fibers and is larger than the fiber diameter of the second fibers.

Third fibers having such a fiber diameter have lower rigidity than the first fibers having a relatively large fiber diameter. Accordingly, the topsheet has higher softness, and the warming device has higher texture and higher feeling of use.

The fiber diameter of the third fibers can be determined by substantially the same measurement method as for the fiber diameter of the first fibers while the topsheet is observed in plan view under a scanning electron microscope.

When the first fiber layer 51 includes the first fibers and the third fibers, both the fibers may be in a mixed state, or the first fiber layer 51 may have a multiple layer structure including a layer substantially composed of the first fibers and a layer substantially composed of the third fibers.

In a preferred embodiment, when the topsheet 5 has a two-layer structure including the first fiber layer 51 constituting the non-skin-facing surface and the second fiber layer 52 constituting the skin-facing surface, the fiber diameters of the constituent fibers can be determined, for example, by the following method.

First, two fiber layers are identified by the above measurement method, and histograms are prepared.

For example, in a first fiber layer 51 including only the first fibers, the histogram on the non-skin-facing surface of the measurement sample has only one peak, and thus the fiber diameter at the peak top is the fiber diameter of the first fibers. Meanwhile, in a first fiber layer 51 including the first fibers and the third fibers, the histogram on the non-skin-facing surface of the measurement sample has two peaks. The fiber diameter at a peak located at the larger fiber diameter side of the peaks is the fiber diameter of the first fibers, whereas the fiber diameter at a peak located at the smaller fiber diameter side is the fiber diameter of the third fibers.

In a second fiber layer 52 including only the second fibers, the histogram on the skin-facing surface of the measurement sample has only one peak, and thus the fiber diameter at the peak top is the fiber diameter of the second fibers.

From the viewpoint of improving softness and fitting properties due to bulk recovery when the warming device 1 is used, the mass proportion of the third fibers to the first fiber layer 51 in the topsheet is preferably 10% by mass or more, more preferably 25% by mass or more, and even more preferably 40% by mass or more and is preferably 90% by mass or less, more preferably 75% by mass or less, and even more preferably 60% by mass or less.

From a similar viewpoint, the mass proportion of the first fibers to the first fiber layer 51 in the topsheet is preferably 10% by mass or more, more preferably 25% by mass or more, and even more preferably 40% by mass or more and is preferably 90% by mass or less, more preferably 75% by mass or less, and even more preferably 60% by mass or less.

In the topsheet, the mass ratio of the second fibers to the second fiber layer 52 is preferably 80% by mass or more, more preferably 90% by mass or more, even more preferably 95% by mass or more, and further preferably 100% by mass. In other words, the second fiber layer 52 is preferably composed of only the second fibers except inevitably contained fibers.

With such a structure, when the topsheet comes into contact with the skin, the second fibers having relatively low rigidity are likely to come into contact, and thus good texture or smooth feel is effectively achieved.

The proportions of the first fibers, the second fibers, and the third fibers included in the topsheet 5 can be determined, for example, by the following method.

The proportions of the first fibers and the third fibers are determined as follows: from a first fiber layer 51, 100 fibers are randomly selected under a digital microscope, and the widths in plan view are measured as the fiber diameters. The arithmetic mean value of 100 fiber diameters is then calculated. When the fiber diameter of a fiber differs from the arithmetic mean value by 2 μm or more, the fiber is determined as another fiber, and fibers having a larger fiber diameter than the arithmetic mean value are regarded as the first fibers, whereas fibers having a smaller fiber diameter than the arithmetic mean value are regarded as the third fibers. Fibers having a fiber diameter different from the mean value by less than 2 μm are regarded as the first fibers. After the fiber diameter measurement, the fibers are classified into first fibers and third fibers, which are separately weighed. The proportions of the first fibers and the third fibers in the randomly selected 100 fibers are calculated. Next, each of the first fiber layer 51 and the second fiber layer 52 is cut into a 1 cm×1 cm sample, and the sample is weighed. The proportions of the first fiber layer 51 and the second fiber layer 52 are then calculated. From the above measurement, each proportion of the first fibers, the second fibers, and the third fibers is calculated.

Next, preferred constituent materials for the first fibers, the second fibers, and the third fibers will be described. The first fibers, the second fibers, and the third fibers are each preferably contain a thermoplastic resin from the viewpoint of production convenience and the cost of the warming device.

Examples of the thermoplastic resin used in the respective fibers independently include polyester resins such as polyethylene (PE), polypropylene (PP), polyethylene terephthalate (PET), and polybutylene terephthalate (PBT); ethylene-□-olefin copolymers such as an ethylene-propylene copolymer; vinyl resins such as polyvinyl chloride, polyvinylidene chloride, and polystyrene; acrylic acid resins such as polyacrylic acid, polyacrylic acid ester, polymethacrylic acid, and polymethacrylic acid ester; polyamide resins; and combinations thereof. Other examples include resins disclosed in JP 9-296325 A.

When the above thermoplastic resins are used in combination, a mixture of two or more thermoplastic resins containing different components may be contained in fibers, or two thermoplastic resins containing different components may be contained in fibers in which a clear boundary is formed between the thermoplastic resins, like concentric core-sheath composite fibers, eccentric core-sheath composite fibers, or side-by-side composite fibers containing two thermoplastic resins.

Examples of the combination of the core/the sheath in core-sheath fibers or the combination of the first resin/the second resin in side-by-side composite fibers include fibers containing polypropylene/polyethylene, polypropylene/ethylene-propylene copolymer, polyethylene terephthalate/polyethylene, and polyethylene terephthalate/polypropylene. These combinations may be used singly or in combination of two or more of them.

In the present invention, the type of a thermoplastic resin contained in fibers can be determined by melting point measurement by differential scanning calorimetry (DSC).

The first fibers preferably contain at least a PET resin as described above, are more preferably fibers including only a PET resin or fibers including only a PET resin and an additional thermoplastic resin other than the PET resin, and even more preferably fibers including only a PET resin.

With such a structure, when the warming device is released from a compressed state, the bulk of the topsheet is easily recovered due to the rigidity of the first fibers, and the topsheet can sufficiently maintain a thickness suitable for effectively manifesting softness. In addition, the thickness of the topsheet can be greatly changed to improve the fitting properties when the warming device is used.

The second fibers preferably contain a PE resin, more preferably contain a PET resin or a PP resin in addition to a PE resin, and are even more preferably fibers containing only a PE resin and a PET resin or a PP resin.

With such a structure, fiber fuzz is suppressed on the topsheet, and good smoothness can be sensed on the skin or the like, further improving the feeling of use. This is also advantageous in suppressing fiber fuzz on a sheet that is prepared by heat fusing second fibers having the above structure when heat is applied by air-through processing or the like in a production process of the topsheet. In addition, even when the topsheet is conveyed in a production process of the warming device, generation of fiber peeling-off pieces or fiber falling pieces from the topsheet and particles derived from constituent fibers (hereinafter, also collectively called "paper dust") can be suppressed, or paper dust can be prevented from adhering to the sheet surface. This can suppress roughness on the sheet surface, and a warming device having good tactile sensation can be produced. Moreover, the amount of wasted sheets can be reduced, and the production efficiency can be increased.

When the first fibers further contain an additional thermoplastic resin other than the PET resin, the first fibers are further preferably core-sheath fibers including a PET resin and the additional thermoplastic resin, from the viewpoint of suppressing generation and adhesion of paper dust and of further improving the sheet texture and the feeling of use of the warming device due to an improvement in softness and a reduction in fiber fuzz.

From the viewpoint of suppressing generation and adhesion of paper dust and of further improving the sheet texture and the feeling of use of the warming device due to an improvement in softness and a reduction in fiber fuzz, the second fibers are further preferably core-sheath fibers including a PE resin and another thermoplastic resin.

The third fibers preferably contain a thermoplastic resin other than the PET resin, more preferably contain a PE resin, even more preferably contain a PET resin or a PP resin in addition to a PE resin, and further preferably contain only a PP resin and a PE resin. The second fibers and the third fibers also preferably contain resins different in component.

With such a structure, fiber fuzz is suppressed on the topsheet, and good smoothness can be sensed on the skin or the like, further improving the feeling of use. This is also advantageous in suppressing fiber fuzz on a sheet that is prepared by heat fusing second fibers having the above structure when heat is applied by air-through processing or the like in a production process of the topsheet. In addition, even when the topsheet is conveyed in a production process of the warming device, generation of paper dust or adhesion of paper dust to the sheet surface can be suppressed. This can suppress roughness on the sheet surface, and a warming device having good tactile sensation can be produced. Moreover, the amount of wasted sheets can be reduced, and the production efficiency can be increased.

When the third fibers further contain an additional thermoplastic resin other than the PET resin, the third fibers are further preferably core-sheath fibers including a PP resin and the additional thermoplastic resin, from the viewpoint of suppressing generation and adhesion of paper dust and of further improving the sheet texture and the feeling of use of the warming device due to an improvement in softness and a reduction in fiber fuzz. In the third fibers in the case, the core is preferably a PP resin, and the sheath is preferably a PE resin.

As long as the effect of the invention is achieved, in addition to or in place of the above fibers, the topsheet 5 may include additional fibers other than the fibers containing the thermoplastic resin.

Examples of the additional fibers include natural fibers such as wood pulp, cotton, and hemp, and regenerated fibers such as rayon fibers and cupra rayon fibers. These types of fibers may be used singly or in combination of two or more of types.

Next, items commonly used in the warming device in the disclosure will be described. The sheet materials usable in the heat generating element 3, the ear loop portion 4, the topsheet 5, and the backsheet 6 can be appropriately selected in consideration of characteristics such as breathability, moisture permeability, texture, elasticity, strength, and performance of preventing leakage of constituent materials from the heat generating sheet and the heat generating composition. For example, a fiber sheet such as a nonwoven fabric, a woven fabric, and paper, a resin foam sheet, a metal sheet, or a combination of them may be used.

As the highly breathable sheet material, a meltblown nonwoven fabric is suitably used. As the sheet material used for improving the texture, an air-through nonwoven fabric or a thermally bonded nonwoven fabric is suitably used.

As the sheet material used for manifesting elasticity, for example, an air-through nonwoven fabric, a spunbonded nonwoven fabric, or a thermally bonded nonwoven fabric containing synthetic fibers of a polyester such as polyethylene terephthalate, a polyethylene, a polypropylene, or the like is used.

As the sheet material used for imparting strength, a spunbonded nonwoven fabric, a spunlace nonwoven fabric, a needle punching nonwoven fabric, a chemically bonded nonwoven fabric, or the like is suitably used.

In addition to or in place of the above nonwoven fabric, a nonwoven fabric that has been surface-treated with a silicone, a surfactant, or the like may be used, or a foam sheet prepared from a thermoplastic resin such as polyethylene and polyurethane may be used. For such a sheet material, multiple types of fibers different in fiber material, fiber diameter, fiber crimping degree, or the like may be mixed, or multiple sheet materials may be combined, and intended characteristics may be manifested.

The heat generating element 3, the ear loop portion 4, the topsheet 5, and the backsheet 6 may have a single structure composed of only one sheet material regardless of a single layer or multiple layers or may have a multiple layer structure in which two or more sheet materials are laminated.

As the topsheet 5, a fiber sheet is preferably used as described above, and at least one of a needle punching nonwoven fabric, an air-through nonwoven fabric, a spunbonded nonwoven fabric, and a chemically bonded nonwoven fabric can be preferably used from the viewpoint of easily preparing a fiber sheet containing a thermoplastic resin. When the topsheet 5 is a laminate of sheet materials, and each sheet material contains crimped fibers, the respective sheet materials independently satisfy a crimp ratio and the number of crimps.

When a breathable fiber sheet is used as the topsheet 5, the air permeance of the topsheet 5 is preferably 0.01 sec/100 mL or more, more preferably 50 sec/100 mL or more, and even more preferably 2,000 sec/100 mL or more. The air permeance of the topsheet 5 is preferably 15,000 sec/100 mL or less, more preferably 50,000 sec/100 mL or less, and even more preferably 10,000 sec/100 mL or less. The air permeance is determined by the method described in JIS P8117. A small air permeance means that air does not take long time to pass or means high breathability.

When a nonwoven fabric is used as the backsheet 6, a fiber sheet having a higher air permeance than the topsheet 5 is preferably used. In other words, the backsheet 6 preferably has a larger air permeance than the topsheet 5 as determined by the method described in JIS P8117. Specifically, the backsheet 6 preferably has a higher air permeance, and the air permeance is preferably 50 sec/100 mL or more, more preferably 4,000 sec/100 mL or more, and even more preferably 20,000 sec/100 mL or more, provided that the backsheet 6 has a larger air permeance than the topsheet 5. The backsheet is further preferably an air impermeable sheet.

When nonwoven fabrics are used as the topsheet 5 and the backsheet 6, the basis weight of the topsheet 5 is preferably 10 g/m$^2$ or more, more preferably 20 g/m$^2$ or more, and even more preferably 30 g/m$^2$ or more as the basis weight of the whole sheet. The basis weight of the topsheet 5 is preferably 200 g/m$^2$ or less, more preferably 130 g/m$^2$ or less, and even more preferably 90 g/m$^2$ or less. With such a structure, both the sheet thickness and the softness can be satisfied, and good touch feeling and fitting properties can be achieved.

When the topsheet 5 has the first fiber layer 51, the basis weight of the first fiber layer 51 is preferably 10 g/m$^2$ or more, more preferably 15 g/m$^2$ or more, and even more preferably 20 g/m$^2$ or more. The basis weight of the first fiber layer 51 is preferably 100 g/m$^2$ or less, more preferably 80 g/m$^2$ or less, and even more preferably 60 g/m$^2$ or less. With such a structure, when the packing bag is opened to release the compressed state, the bulk of the topsheet is easily recovered, and the thickness can be greatly changed immediately after use. Accordingly, high fitting properties, high feeling of use, and good texture are achieved.

When the topsheet 5 has the second fiber layer 52, the basis weight of the second fiber layer 52 is preferably 5 g/m$^2$ or more, more preferably 10 g/m$^2$ or more, and even more preferably 15 g/m$^2$ or more. The basis weight of the second fiber layer 52 is preferably 50 g/m$^2$ or less, more preferably 40 g/m$^2$ or less, and even more preferably 30 g/m$^2$ or less. With such a structure, high-rigidity fibers such as the first fibers included in the first fiber layer 51 are prevented from unintentionally sticking through the second fiber layer 52 or the skin-facing surface, and good smoothness of the sheet surface can be achieved on a surface to come into contact with a heating object such as the skin.

When the topsheet 5 has the first fiber layer 51, the number of fibers present in the unit volume of the first fiber layer 51 is preferably 1,500 pieces/cm$^2$ or less, more preferably 1,000 pieces/cm$^2$ or less, and even more preferably 700 pieces/cm$^2$ or less and is practically 150 pieces/cm$^2$ or more. With such a structure, the sheet has a larger thickness, and good fitting properties can be achieved.

When the topsheet 5 has the second fiber layer 52, the number of fibers present in the unit volume of the second fiber layer 52 is preferably 200 pieces/cm$^2$ or more, more preferably 300 pieces/cm$^2$ or more, and even more preferably 400 pieces/cm$^2$ or more and is preferably 1,500 pieces/cm$^2$ or less, more preferably 1,200 pieces/cm$^2$ or less, and even more preferably 1,000 pieces/cm$^2$ or less.

With such a structure, relatively high-rigidity fibers such as the first fibers and the third fibers included in the first fiber layer 51 are prevented from unintentionally sticking through the second fiber layer 52 or the skin-facing surface, and good smoothness of the sheet surface can be achieved on a surface to come into contact with a heating object such as the skin.

From the viewpoint of achieving such effects, the number of fibers present in the unit volume of the second fiber layer 52 is preferably larger than the number of fibers present in the unit volume of the first fiber layer.

The number of fibers present in the unit volume of the topsheet 5 can be determined by the following method.

First, a cross section of the measurement sample prepared by the above method is observed under a microscope or an SEM, and a difference in fiber diameter or fiber structure is ascertained to identify two fiber layers. Then, from the measurement sample, a first fiber layer and a second fiber layer are separated, and the number of fibers in a 1 cm×1 cm cut sheet is counted by SEM observation. The counted number of fibers is calculated as the number of fibers present in 1 $cm^2$.

As for the basis weight of the backsheet 6, from the viewpoint of improving heat retaining properties in an intended area when the warming device is used, the basis weight of the backsheet 6 is preferably 10 $g/m^2$ or more and more preferably 30 $g/m^2$ or more in terms of total basis weight. The basis weight of the backsheet 6 is preferably 200 $g/m^2$ or less and more preferably 150 $g/m^2$ or less.

The topsheet 5 preferably has a thickness within a predetermined range at the starting point of heat generation. Specifically, at the starting point of heat generation of the warming device, the thickness of the topsheet 5 is preferably 1.8 mm or more, more preferably 2.5 mm or more, and even more preferably 3.5 mm or more and is preferably 6.0 mm or less, more preferably 5.5 mm or less, and even more preferably 5.0 mm or less.

Having such a thickness means that the bulk of the topsheet 5 can be recovered immediately after use. Accordingly, good softness and texture can be achieved immediately after start of use of the warming device, and fitting properties to a heating object can be improved.

The thickness of the topsheet 5 10 minutes after the starting point of heat generation by the warming device is preferably 1.7 mm or more, more preferably 3.0 mm or more, even more preferably 4.0 mm or more, and further preferably 4.5 mm or more and is preferably 8.0 mm or less, more preferably 7.0 mm or less, and even more preferably 6.5 mm or less.

Having such a thickness means that the bulk of the topsheet 5 can be recovered and maintained during use. Accordingly, good softness and texture can be achieved over a long time during the use of the warming device, and fitting properties to a heating object can be improved.

The thickness of a topsheet 5 and the thickness increase amount can be determined by the following method for a warming device 1 that is before heat generation and is packed and sealed in a packing bag or the like.

In a warming device that is before heat generation and is packed and sealed in a package or the like, a load of 3.7 $gf/cm^2$ is applied to a sheet; thicknesses are measured at three or more points by using a constant pressure thickness gauge or the like; and the arithmetic mean value is calculated as the sheet thickness T1 (mm) at the starting point of heat generation. Similarly, the sheet thicknesses are measured in a similar manner under the same load 10 minutes after the starting point of heat generation, and the arithmetic mean value is calculated as the sheet thickness T2 (mm) at 10 minutes.

In the measurement, the time from the start of opening a packing bag or the like until a warming device 1 is exposed to an oxygen-containing atmosphere such as air and from the start of opening until a topsheet 5 is spread and placed on a flat table, or the time point 30 seconds after the start of opening is defines as the "starting point of heat generation". At the time, in the topsheet 5 of the embodiment, the thickness of the topsheet 5 preferably increases or is preferably maintained.

In the disclosure, "generating vapor" means that the total generation amount of water vapor for 10 minutes is 10 mg or more/10 min as determined by the following method. The water vapor generation amount can be easily achieved by using, as the heat generating portion 3*a*, a paste-like substance containing an oxidizable metal, a carbon material, and water, for example.

Figure 6:
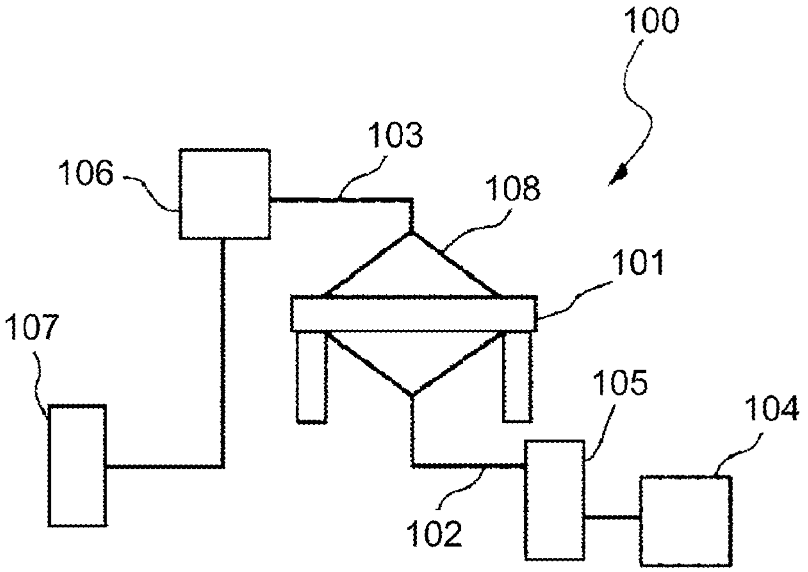
FIG. 6 is a schematic view of an apparatus for determining the amount of vapor generated from a warming device.

To determine the water vapor generation amount, for example, an apparatus 100 having the structure shown in FIG. 6 can be used. The apparatus 100 includes an aluminum measuring chamber 101 (a volume of 4.2 L), an inlet passage 102 connected to the lower part of the measuring chamber 101, and an outlet passage 103 connected to the upper part of the measuring chamber 101. The inlet passage 102 is configured to allow dehumidified air (a humidity of less than 2% RH, a flow rate of 2.1 L/min) supplied from an air supply unit (not shown) to flow into the measuring chamber 101. The apparatus 100 further includes an inlet thermo-hygrometer 104 and an inlet flowmeter 105 on the inlet passage 102, an outlet thermo-hygrometer 106 and an outlet flowmeter 107 on the outlet passage 103, and a thermometer (thermistor) 108 in the measuring chamber 101. As the thermometer 108, a thermometer having a temperature resolution of about 0.01° C. is preferably used.

The method of measuring the total generation amount of water vapor by using the apparatus 100 will be described below.

First, for a warming device that is packed in an oxygen barrier bag and is to be measured, the oxygen barrier bag is opened, and one heat generating element is taken out. When a heat generating element is stored in a bag, the heat generating element is taken out together with the bag.

The taken out heat generating element is placed in the measuring chamber 101 such that one face of the bag faces outward, and the thermometer 108 is placed thereon. When one face and the other face of a bag include sheet materials different in breathability, the bag is placed in the measuring chamber 101 such that the face of the sheet material having higher breathability in the bag faces outward, and the thermometer 108 is placed on the face.

In this condition, dehumidified air is allowed to flow from the lower part of the measuring chamber 101 through the inlet passage 102. From the temperatures and the humidities each measured with the inlet thermo-hygrometer 104 or the outlet thermo-hygrometer 106, the difference in absolute humidity before and after the air passage through the measuring chamber 101 is calculated. Moreover, from the air flow rates measured with the inlet flowmeter 105 and the outlet flowmeter 107, the water vapor amount discharged from the heat generating element is calculated. The total water vapor amount is the total amount measured for 10 minutes (mg/10 min) from the measurement start point when a warming device is taken out of an oxygen barrier bag, and a heat generating element is brought into contact with air.

Figure 7:
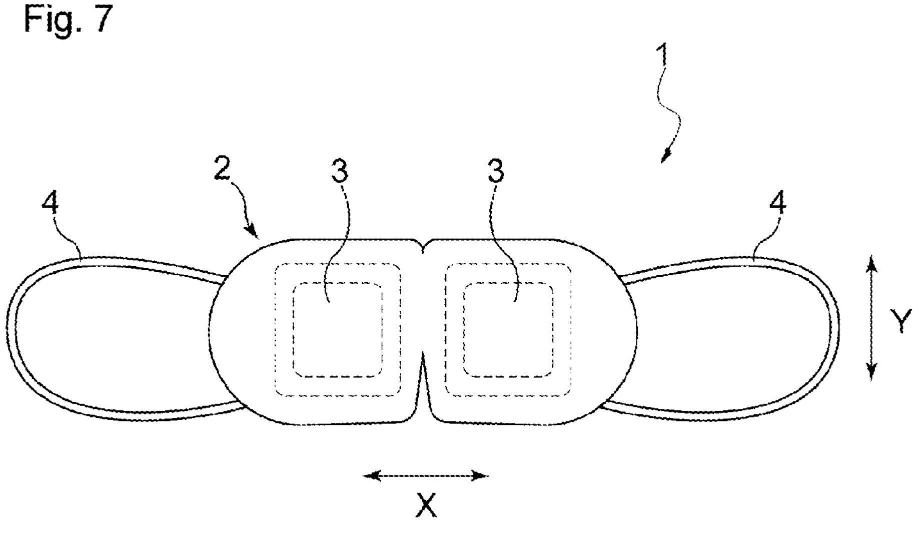
FIG. 7 is a plan view showing another embodiment of the warming device of the present invention.

In the warming device 1, the ear loop portion 4 may have any shape that can fix the main body 2 to the eyes of a user and is not limited to the sheet-shaped member shown in FIG. 1 and FIG. 2. For example, as shown in FIG. 7, ear loop portions 4 including string-like members may be adopted, or ear loop portions 4 including thready or strip-shaped members may be adopted. From the viewpoint of improving fitting properties of the warming device, an elastic body such as rubber is preferably used to prepare stretchable ear loop portions 4.

The form of the heat generating element 3 in the above warming device 1 has been described as a form in which two heat generating elements 3 are spaced and held, but the warming device may be in any form that can give warm feeling to the eyes of a user and around the eyes. For example, a single heat generating element having such a shape and dimensions as to cover the eyes of a user and around the eyes may be interposed between the topsheet 5 and the backsheet 6, or three or more heat generating elements may be interposed between the topsheet 5 and the backsheet 6.

The heat generating element 3 shown in FIG. 2 and FIG. 3 is partly fixed to the center region in the lateral direction X of the warming device 1, but the fixing manner is not limited to this. For example, the heat generating element 3 and the backsheet 6 may be joined continuously or intermittently in the center region and a region other than the center region through an adhesive, or an adhesive may be applied entirely onto an area of the backsheet 6 where the heat generating element 3 is provided, to join them.

The disclosure also provides a warming device package including a packing bag and a warming device packed in the packing bag.

The packing bag, for example, includes an oxygen impermeable sheet material. As the sheet material, a resin film may be used singly, or a laminate of the resin film and a thin film of a metal such as aluminum may be used. This can improve light shielding and airtightness when a warming device is packed.

When a warming device is in a package form, the warming device 1 is preferably stored in a packing bag while a predetermined pressure is applied.

Specifically, the pressure applied to the warming device in the package is preferably 500 Pa or more, more preferably 1,000 Pa or more, and even more preferably 2,000 Pa or more from the viewpoint of reducing the space of the package during storage and distribution.

From the viewpoint of easily recovering the bulk of the sheet laminate after opening the packing bag, the above pressure is preferably 5,000 Pa or less, more preferably 4,000 Pa or less, and even more preferably 3,000 Pa or less.

The above warming device can be produced, for example, by the following method. The method for producing the warming device includes producing a topsheet.

An embodiment of the production process of the topsheet, for example, includes a step of blowing hot air to a fiber web including any fibers to make the fiber web into a nonwoven fabric. The step is what is called air-through processing.

To produce, as a preferred embodiment of the topsheet, a topsheet having a two-layer structure that includes a first fiber layer 51 including first fibers and a second fiber layer 52 including second fibers, the following method can be adopted, for example.

First, a fiber web including only first fibers or including a mixture of first fibers and third fibers (hereinafter also called a “first fiber web”) and a fiber web including only second fibers (hereinafter also called a “second fiber web”) are laminated to give a laminate. The laminate is then subjected to air-through processing by blowing hot air, and an intended topsheet is prepared. The topsheet is classified into what is called an air-through nonwoven fabric and is a breathable fiber sheet. The topsheet produced as above typically has a long strip shape and may be cut into a predetermined size as needed.

As in the above preferred embodiment, when a laminate including second fibers or third fibers is heated by air-through processing or the like in the production process of a topsheet, fibers including first fibers containing a PET resin are heat fused to each other, and fiber fuzz can be reduced on the prepared sheet advantageously. Many fused points of fibers included in a topsheet are formed, and thus even when the topsheet is conveyed in the subsequent production process of a warming device, generation of paper dust can be reduced. This can suppress roughness on the sheet surface, and a warming device having good tactile sensation can be produced at high productivity. In addition, the amount of wasted sheets that fail to satisfy required quality due to paper dust can be reduced, and the environmental load can be reduced.

The above fiber webs can be produced by a known web forming method such as carding.

When the topsheet includes a single fiber layer (has a single layer structure), the above method can be performed by using only the first fiber web. When the topsheet includes three or more fiber layers, the first fiber web and the second fiber web as well as an additional fiber web including other fibers may be laminated into a laminate, and hot air may be blown to the laminate.

Alternatively, the above topsheet may be prepared by subjecting a fiber web or a laminate thereof to needle punching. The prepared topsheet as above is classified into what is called a needle punching nonwoven fabric and is a breathable fiber sheet.

The topsheet produced as above is conveyed to be subjected to the following processing, and through predetermined processing, a warming device is produced.

In the method for producing a warming device, for example, an adhesive is applied onto one surface of at least one of a topsheet and a backsheet while the topsheet and the backsheet are each conveyed in the same direction. As for the application method of an adhesive, an adhesive may be applied continuously or intermittently in the sheet conveyance direction and may be applied continuously or intermittently also in a direction orthogonal to the conveyance direction. An adhesive may also be applied so as to form adhesive uncoated areas.

Next, on the adhesive coated face of the sheet with an adhesive, heat generating elements 3 produced separately are stacked. On the heat generating elements 3, the other sheet is further stacked, and the sheets 5, 6 are joined through the adhesive. Through the step, a main body 2 in which the heat generating elements 3 are interposed between the topsheet 5 and the backsheet 6 is produced. To join the sheets 5, 6, for example, a laminate including the first sheet 5, the heat generating elements 3, and the second sheet 6 may be introduced between a pair of pressing rolls and pressed to improve the joint.

The present invention has been described on the basis of preferred embodiments thereof, but the present invention is not limited to the above embodiments.

In consideration of the above embodiments, the following warming devices will be disclosed.

<1>

A warming device including a topsheet to be located close to a skin of a user, a backsheet to be located far from the skin of the user, and a heat generating element interposed between the topsheet and the backsheet, in which

- the heat generating element contains an oxidizable metal, a carbon material, an electrolyte, and water,
- the heat generating element is configured to generate vapor from the heat generating element itself as heat is generated,
- the topsheet includes a breathable fiber sheet including fibers containing at least a polyethylene terephthalate resin, and
- the topsheet contains first fibers having a fiber diameter of more than 15 μm in plan view as measured by observation under a scanning electron microscope.

<2>

The warming device as set forth in clause <1>, in which the fiber diameter of the first fibers is more preferably 20 μm or more and even more preferably 25 μm or more and is preferably 60 μm or less, more preferably 50 μm or less, even more preferably 45 μm or less, further preferably 40 μm or less, and furthermore preferably 30 μm or less.

<3>

The warming device as set forth in clause <1> or <2>, in which the first fibers are more preferably fibers containing only the polyethylene terephthalate resin or fibers containing only the polyethylene terephthalate resin and a thermoplastic resin other than the polyethylene terephthalate resin, and the first fibers are even more preferably fibers containing only a polyethylene terephthalate resin.

<4>

The warming device as set forth in any one of clauses <1> to <3>, in which the first fibers are core-sheath fibers in which the core is the polyethylene terephthalate resin, and the sheath is a polyethylene resin.

<5>

The warming device as set forth in any one of clauses <1> to <4>, in which the topsheet has a multiple layer structure including a first fiber layer and a second fiber layer, only one of the fiber layers contains the first fibers, and fibers having a fiber diameter different from that of the first fibers are contained in the fiber layer containing no first fibers.

<6>

The warming device as set forth in clause <5>, in which the topsheet has a two-layer structure including only the first fiber layer and the second fiber layer.

<7>

The warming device as set forth in clause <5> or <6>, in which the first fiber layer includes the first fibers, and the second fiber layer includes second fibers having a smaller fiber diameter than the first fibers and having a fiber diameter of 6 μm or more and 30 μm or less.

<8>

The warming device as set forth in clause <7>, in which the fiber diameter of the second fibers is smaller than the fiber diameter of the first fibers, and the fiber diameter of the second fibers is preferably 10 μm or more and more preferably 13 μm or more, and is preferably 25 μm or less, more preferably 20 μm or less, and even more preferably 17 μm or less.

<9>

The warming device as set forth in clause <7> or <8>, in which the second fibers preferably contain a polyethylene resin, more preferably contain a polyethylene resin and a polyethylene terephthalate resin or a polypropylene resin, and even more preferably contain only a polyethylene resin and the polyethylene terephthalate resin or a polypropylene resin, and the second fibers have the fiber diameter of 6 μm or more and 30 μm or less.

<10>

The warming device as set forth in any one of clauses <7> to <9>, in which the second fibers are core-sheath fibers in which the core is a polyethylene terephthalate resin or a polypropylene resin, and the sheath is a polyethylene resin.

<11>

The warming device as set forth in any one of clauses <5> to <10>, in which the first fiber layer is provided at the side far from the skin of a user when the warming device is used, and the second fiber layer is provided on a skin-contact surface when the warming device is used.

<12>

The warming device as set forth in any one of clauses <5> to <11>, in which the first fiber layer further contains third fibers having a smaller fiber diameter than the fiber diameter of the first fibers and having a larger fiber diameter than the fiber diameter of the second fibers.

<13>

The warming device as set forth in clause <12>, in which the fiber diameter of the third fibers is preferably 15 μm or more, more preferably 18 μm or more, and even more preferably 20 μm or more and is preferably 50 μm or less, more preferably 40 μm or less, even more preferably 30 μm or less, and further preferably 24 μm or less, provided that the fiber diameter of the third fibers is smaller than the fiber diameter of the first fibers and is larger than the fiber diameter of the second fibers.

<14>

The warming device as set forth in clause <12> or <13>, in which the third fibers preferably contain a thermoplastic resin other than the polyethylene terephthalate resin, more preferably contain a polyethylene resin, even more preferably contain a polyethylene resin and a PET resin or a PP resin, and further preferably contain only a PP resin and a PE resin, and the fiber diameter of the third fibers is smaller than the fiber diameter of the first fibers and is larger than the fiber diameter of the second fibers.

<15>

The warming device as set forth in any one of clauses <12> to <14>, in which the third fibers are core-sheath fibers in which the core is a polyethylene terephthalate resin or a polypropylene resin, and the sheath is a polyethylene resin.

<16>

The warming device as set forth in any one of clauses <12> to <15>, in which the second fiber layer includes the second fibers, and the second fibers and the third fibers contain resins different in component.

<17>

The warming device as set forth in any one of clauses <12> to <16>, in which the first fibers are fibers containing only the polyethylene terephthalate resin and a thermoplastic resin other than the polyethylene terephthalate resin, and the third fibers are fibers containing a thermoplastic resin other than the polyethylene terephthalate resin.

<18>

The warming device as set forth in any one of clauses <12> to <17>, in which the mass proportion of the third fibers to the total mass of the first fiber layer is preferably 10% by mass or more, more preferably 25% by mass or more, and even more preferably 40% by mass or more and is preferably 90% by mass or less, more preferably 75% by mass or less, and even more preferably 60% by mass or less.

<19>

The warming device as set forth in any one of clauses <12> to <18>, in which the mass proportion of the first fibers to the total mass of the first fiber layer is preferably 10% by mass or more, more preferably 25% by mass or more, and even more preferably 40% by mass or more and is preferably 90% by mass or less, more preferably 75% by mass or less, and even more preferably 60% by mass or less.

<20>

The warming device as set forth in any one of clauses <5> to <19>, in which the first fiber layer includes first fibers containing the polyethylene terephthalate resin and a polyethylene resin.

<21>

The warming device as set forth in any one of clauses <5> to <20>, in which the second fiber layer includes the second fibers, and the content of the second fibers in the second fiber layer is preferably 80% by mass or more, more preferably 90% by mass or more, even more preferably 95% by mass or more, and further preferably 100% by mass.

<22>

The warming device as set forth in any one of clauses <5> to <21>, in which the number of fibers present in the unit volume of the first fiber layer is preferably 1,500 pieces/cm$^2$ or less, more preferably 1,000 pieces/cm$^2$ or less, and even more preferably 700 pieces/cm$^2$ or less and is 150 pieces/cm$^2$ or more.

<23>

The warming device as set forth in any one of clauses <5> to <22>, in which a number of fibers present in a unit volume of the second fiber layer is 200 pieces/cm$^2$ or more and 1,500 pieces/cm$^2$ or less.

<24>

The warming device as set forth in any one of clauses <5> to <23>, in which the number of fibers present in the unit volume of the second fiber layer is more preferably 300 pieces/cm$^2$ or more and even more preferably 400 pieces/cm$^2$ or more and is preferably 1,200 pieces/cm$^2$ or less and more preferably 1,000 pieces/cm$^2$ or less.

<25>

The warming device as set forth in any one of clauses <5> to <24>, in which the first fiber layer includes, except inevitably contained other fibers, only the first fibers and third fibers having a smaller fiber diameter than the fiber diameter of the first fibers, the second fiber layer includes, except inevitably contained other fibers, only the second fibers having a smaller fiber diameter than the first fibers and having a fiber diameter of 6 μm or more and 30 μm or less, and the fiber diameter of the third fiber is larger than the fiber diameter of the second fibers.

<26>

The warming device as set forth in any one of clauses <5> to <25>, in which a basis weight of the first fiber layer is preferably 10 g/m$^2$ or more, more preferably 15 g/m$^2$ or more, and even more preferably 20 g/m$^2$ or more and is preferably 100 g/m$^2$ or less, more preferably 80 g/m$^2$ or less, and even more preferably 60 g/m$^2$ or less.

<27>

The warming device as set forth in any one of clauses <5> to <26>, in which the basis weight of the second fiber layer is preferably 5 g/m$^2$ or more, more preferably 10 g/m$^2$ or more, and even more preferably 15 g/m$^2$ or more and the basis weight of the second fiber layer is preferably 50 g/m$^2$ or less, more preferably 40 g/m$^2$ or less, and even more preferably 30 g/m$^2$ or less.

<28>

The warming device as set forth in any one of clauses <1> to <27>, in which the topsheet is a fiber sheet in the sheet form that is maintained by at least one of fusion and entanglement of constituent fibers, and the topsheet has contact parts at which the constituent fibers are in contact with each other.

<29>

The warming device as set forth in clause <28>, in which the fiber sheet is an air-through nonwoven fabric or a needle punching nonwoven fabric.

<30>

The warming device as set forth in any one of clauses <1> to <29>, in which the topsheet has a thickness of 1.8 mm or more and 6.0 mm or less at the starting point of heat generation of the warming device.

<31>

The warming device as set forth in any one of clauses <1> to <30>, in which the heat generating element includes a layer containing the oxidizable metal, the carbon material, the electrolyte, and the water and includes, adjacent to the layer, a humectant layer containing a water absorbing polymer.

<32>

A method for producing the warming device as set forth in any one of clauses <1> to <27>, comprising a step of producing the topsheet, wherein in the step, a laminate of a web of fibers containing a polyethylene terephthalate resin and a web containing fibers other than the above fibers is subjected to air-through processing.

EXAMPLES

The present invention will next be described in further detail with reference to examples. However, the scope of the invention is not limited to the examples.

Fiber diameters and the number of fibers were determined by SEM observation of a sample topsheet in plan view while fibers were observed at a magnification of 2,000×. The observation was then repeated until the number of fibers reached 100 or more while the SEM observation region was changed, and the number of layers in a topsheet was identified. In the observation, an image analysis software (Photoshop, Adobe) was used to color-code fibers, and the dimensions were measured. Then, the range of a fiber diameter class was selected from a range of 0.1 to 0.5 μm, and a histogram of the frequency of the number of fibers and the distribution of fiber diameters was prepared on the basis of the measurement result. From the number of peaks, whether a topsheet contains a single type of fibers or multiple types of fibers was determined. In each of Examples and Comparative Example, the type of fibers and the mass proportion of fibers in a fiber layer were determined from the number of layers in a topsheet and the fiber diameter in each layer.

Unless otherwise noted, "%" in the following description means "% by mass."

Example 1

A first fiber web (basis weight: 40 g/m$^2$) including 100% by mass of first fibers that were core-sheath fibers in which the core was a PET resin, and the sheath was a PE resin (50% by mass of each resin) and a second fiber web including 100% by mass of second fibers that were core-sheath fibers in which the core was a PET resin, and the sheath was a PE resin (50% by mass of each resin) were laminated to give a laminate. The laminate was subjected to air-through processing to give a topsheet 5 (air-through nonwoven fabric, basis weight: 60 g/m$^2$) having a two-layer structure of the first fiber layer 51 and the second fiber layer 52.

As a backsheet 6, a single layer of an air-through nonwoven fabric (basis weight: 30 g/m$^2$, manufactured by Kinsei Seishi) including fibers containing only a thermoplastic resin was used.

The number of layers in the topsheet: 2

First fiber layer: 100% of fibers having a fiber diameter of 22 μm

Second fiber layer: 100% of fibers having a fiber diameter of 15 μm

Separately, a heat generating element 3 to generate vapor with heat generation was produced. First, to an aqueous solution in which sodium chloride as an electrolyte and a thickener were dissolved in water, iron powder as an oxidizable metal was added, and the whole was stirred. Activated carbon as a carbon material was further added, and the whole was thoroughly stirred until a homogeneous dispersion was prepared, giving a paste-like heat generating composition.

Onto a tissue paper laminated with polyethylene, the above paste-like heat generating composition was applied at a basis weight of 600 g/m$^2$. Next, on the heat generating composition, particles of a water absorbing polymer (Aqualic (registered trademark) CA, manufactured by Nippon Shokubai) were sprayed as a water retention agent in layers at a basis weight of 70 g/m$^2$. On the water absorbing polymer layer, a crepe paper (a basis weight of 65 g/m$^2$) was laminated to give a heat generating portion 3*a* including a water retention agent layer.

The heat generating portion 3*a* was next cut into a size of 50 mm×50 mm. The heat generating element was sandwiched between a moisture permeable sheet and a moisture impermeable sheet cut in a size of 63 mm×63 mm, and four sides of the sheets were heat-packed to give a heat generating element 3 in which the heat generating portion 3*a* was stored in a bag 3*b*.

The topsheet 5 was placed such that the first fiber layer 51 faced the heat generating element 3, and the second fiber layer 52 was to be in contact with a heating object. The moisture permeable sheet of the bag 3*b* was placed so as to face the topsheet 5.

The members were placed as above and were joined such that the heat generating element 3 configured to generate vapor with heat generation was stored between the above sheets 5, 6, and a warming device having the structure shown in FIG. 1 to FIG. 3 and FIG. 5 was produced.

Examples 2 to 4

As shown in Table 1, the type or the constitution ratio of fibers included in the topsheet 5 were changed. Specifically, a mixture of first fibers containing only a PET resin and third fibers in which the core was a PP resin, and the sheath was a PE resin (Example 2) or in which the core was a PET resin, and the sheath was a PE resin (Examples 3 and 4) was supplied to a carding machine, and a mixed fiber web including the first fibers and the third fibers was prepared as a first fiber web. A similar procedure to that in Example 1 was performed except the above to give a warming device including a topsheet 5 that was an air-through nonwoven fabric having a two-layer structure.

Example 2

The number of layers in the topsheet: 2

First fiber layer: 30% of fibers having a fiber diameter of 27 μm and 70% of fibers having a fiber diameter of 22 μm Second fiber layer: 100% of fibers having a fiber diameter of 15 μm

Example 3

The number of layers in the topsheet: 2

First fiber layer: 30% of fibers having a fiber diameter of 27 μm and 70% of fibers having a fiber diameter of 22 μm Second fiber layer: 100% of fibers having a fiber diameter of 15 μm

Example 4

The number of layers in the topsheet: 2

First fiber layer: 50% of fibers having a fiber diameter of 27 μm and 50% of fibers having a fiber diameter of 22 μm Second fiber layer: 100% of fibers having a fiber diameter of 15 μm

Example 5

As shown in Table 1, the type or the constitution ratio of fibers included in the topsheet 5 were changed. Specifically, a similar procedure to that in Example 1 was performed except a second fiber web including 100% by mass of second fibers that were core-sheath fibers in which the core was a PP resin, and the sheath was PE resin (50% by mass of each resin) was used, giving a warming device including a topsheet 5 that was an air-through nonwoven fabric having a two-layer structure.

The number of layers in the topsheet: 2

First fiber layer: 50% of fibers having a fiber diameter of 27 μm and 50% of fibers having a fiber diameter of 22 μm Second fiber layer: 100% of fibers having a fiber diameter of 12 μm

Example 6

As shown in Table 1, the type or the constitution ratio of fibers included in the topsheet 5 were changed. Specifically, a mixture of first fibers in which the core was a PET resin, and the sheath was a PE resin and third fibers in which the core was a PP resin, and the sheath was a PE resin was supplied to a carding machine, and a mixed fiber web including the first fibers and the third fibers was prepared as a first fiber web. A similar procedure to that in Example 1 was performed except the above to give a warming device including a topsheet 5 that was an air-through nonwoven fabric having a two-layer structure.

Example 6

The number of layers in the topsheet: 2

First fiber layer: 50% of fibers having a fiber diameter of 27 μm and 50% of fibers having a fiber diameter of 22 μm Second fiber layer: 100% of fibers having a fiber diameter of 15 μm

Example 7

A similar procedure to that in Example 1 was performed except that, as shown in Table 1, the type or the constitution ratio of fibers included in the topsheet 5 were changed, core-sheath fibers containing a PET resin/a PE resin and having a fiber diameter different from that in Example 5 were used as first fibers, and an air-through nonwoven fabric containing only the first fibers and having a single layer was used as the topsheet 5, giving a warming device.

Example 7

The number of layers in the topsheet: 1
First fiber layer: 100% of fibers having a fiber diameter of 22 μm Example 8

As shown in Table 1, first fibers (basis weight: 20 g/$m^2$) that were core-sheath fibers in which the core was a PET resin, and the sheath was a PE resin (50% by mass of each resin) and third fibers (basis weight: 20 g/$m^2$) in which the core was a PP resin, and the sheath was a PE resin were mixed to give a first fiber web (total basis weight: 40 g/$m^2$). The first fibers used in the example had a fiber diameter different from that used in Example 1.

Separately, a second fiber web (basis weight: 20 g/$m^2$) including 100% by mass of second fibers that were core-sheath fibers in which the core was a PP resin, and the sheath was PE resin (50% by mass of each resin) was used.

A similar procedure to that in Example 1 was performed except that these fiber webs were used, giving a warming device including a topsheet 5 that was an air-through non-woven fabric having a two-layer structure.

Example 8

The number of layers in the topsheet: 2
First fiber layer: 50% of fibers having a fiber diameter of 40 μm and 50% of fibers having a fiber diameter of 22 μm
Second fiber layer: 100% of fibers having a fiber diameter of 15 μm Example 91

As shown in Table 1, the type or the constitution ratio of fibers included in the topsheet 5 were changed to prepare a first fiber web containing only first fibers that were core-sheath fibers containing only a PET resin, and the first fiber web was subjected to needle punching to give a topsheet 5 having a single layer structure as a needle punching non-woven fabric. A similar procedure to that in Example 1 was performed except the above to give a warming device.

Example 9

The number of layers in the topsheet: 1
First fiber layer: 100% of fibers having a fiber diameter of 19 μm Example 10

As shown in Table 1, the type or the constitution ratio of fibers included in the topsheet 5 were changed. Specifically, a mixture of first fibers containing only a PET resin and third fibers in which the core was a PP resin, and the sheath was a PE resin was supplied to a carding machine, and a mixed fiber web including the first fibers and the third fibers was prepared as a first fiber web. A similar procedure to that in Example 1 was performed except the above to give a warming device including a topsheet 5 that was an air-through nonwoven fabric having a two-layer structure.

Example 10

The number of layers in the topsheet: 2
First fiber layer: 60% of fibers having a fiber diameter of 27 μm and 40% of fibers having a fiber diameter of 22 μm
Second fiber layer: 100% of fibers having a fiber diameter of 15 μm Comparative Example 1

As shown in Table 1, a mixture of first fibers that were core-sheath fibers in which the core was a PP resin, and the sheath was a PE resin and third fibers containing only a PP resin was used to prepare a fiber web, and the fiber web was subjected to needle punching to give a topsheet 5 having a single layer structure of a needle punching nonwoven fabric. A similar procedure to that in Example 1 was performed except the above to give a warming device.

Comparative Example 1

The number of layers in the topsheet: 1
First fiber layer: 30% of fibers having a fiber diameter of 22 μm and 70% of fibers having a fiber diameter of 12 μm

[Measurement of Sheet Thickness and Thickness Increase Amount]

For each warming device in Examples and Comparative Example, the thickness T1 (mm) of the topsheet 5 at the starting point of heat generation and the sheet thickness T2 (mm) 10 minutes after the starting point of heat generation were each measured and calculated. Each measurement environment was in a room at a temperature of 26° C. and a relative humidity of 50%.

Specifically, each warming device in Examples and Comparative Example was packed and sealed in a packing bag, and then the packing bag was opened to expose the warming device to an oxygen-containing atmosphere such as air. Next, from the warming device, only the topsheet 5 was so carefully cut out into a 1.5-cm square measurement sample as not to press the sheet in the thickness direction, and the measurement sample was placed on a flat plate of a digital microscope (VHX-1000 manufactured by KEYENCE) while the cross section of the sheet faced 90 degrees upward. The operation was performed within 30 seconds of the start of opening the packing bag. At the time point 30 seconds after the start of opening, the digital microscope was used to measure the dimension from one side to the other side of the cross section of the sheet at three or more positions, and the arithmetic mean value was calculated as the sheet thickness T1 (mm) at the starting point of heat generation. In a similar manner, from the warming device after 10 minutes, the topsheet 5 was so carefully cut out into a measurement sample having the above dimensions as not to press the sheet, and the sheet thickness T2 (mm) 10 minutes after the starting point of heat generation was determined.

A smaller thickness change amount (T2−T1) indicates that the bulk recovery of a topsheet 5 is higher immediately after use, and a warming device 1 has higher fitting properties and feeling of use. The results are shown in Table 1.

[Sensory Evaluation]

For each warming device in Examples and Comparative Example, expert panelists evaluated smooth touch feeling of a topsheet when the panelist touched the sheet by hand, when the panelist wore a warming device, or after use, softness of a topsheet, and fitting properties when the panelist wore a warming device for 20 minutes so as to cover the eyes on the basis of the following criteria. In each evaluation, the arithmetic mean value of evaluation scores by the expert panelists was shown in Table 1 as the evaluation results. In each evaluation result, a higher score indicates that a topsheet to come into contact with the skin has higher smoothness, and a warming device has higher softness and fitting properties.

<Criteria for Topsheet Smoothness>

Score 4: Tactile sensation is very smooth before use and is continuously smooth to end of use, and no fiber fuzz is observed even after use.

Score 3: Tactile sensation is smooth before use and is continuously smooth during use, but fiber fuzz is slightly observed after use.

Score 2: Tactile sensation is smooth before use, but fiber fuzz is sensed during use and after use, and smoothness is inferior.

Score 1: Fiber fuzz is sensed before use, during use, and after use, and smoothness is very poor.

<Criteria for Topsheet Softness>

Score 5: A topsheet is very soft and is firmly in close contact immediately after use to end of use, and the softness and touch feeling are very good.

Score 4: A topsheet is soft and is in close contact immediately after use to end of use, and the sofiness and touch feeling are good.

Score 3: A topsheet has appropriate rigidity and is in such close contact that warmth is felt during use, and the touch feeling is satisfactory.

Score 2: A topsheet is slightly hard and has slightly poor rigidity but is in close contact during use.

Score 1: A topsheet is very hard, has poor rigidity, and lacks adhesiveness during use.

<Criteria for Fitting Properties>

Score 5: When worn, a warming device is firmly in close contact with the eyes and around the eyes and has excellent fitting properties to end of use.

Score 4: When worn, a warming device is in close contact with the eyes and has good fitting properties to end of use.

Score 3: When worn, a warming device is held on the eyes and around the eyes and has satisfactory fitting properties to end of use.

Score 2: When worn, a warming device is insufficiently in close contact with the eyes and has poor fitting properties to end of use.

Score 1: When worn, a warming device is not in close contact with the eyes at all and has very poor fitting properties to end of use.

[Evaluation of Productivity Due to Paper Dust]

When each warming device 1 in Examples and Comparative Example was produced by using an actual apparatus, the wasted paper dust amount was visually observed by expert panelists. A higher score in evaluation result indicates a warming device with higher productivity.

<Productivity>

Score 3: No paper dust is generated during production; no materials are wasted; a good production environment can be maintained; and a warming device is not affected.

Score 2: Paper dust is slightly generated during production; but the amount of wasted materials is not problematic in the production environment; and a warming device is not affected.

Score 1: Paper dust is generated during production; the amount of wasted materials is slightly large in the production environment; but a warming device is not affected.

[Evaluation of Duration at 38° C. and Maximum Temperature Achieved]

The duration at 38° C. and the maximum temperature achieved of each warming device in Examples and Comparative Example were determined by the following method. A longer duration at 38° C. indicates better continuity of heat generation, and a higher maximum temperature achieved indicates better heat generation properties. The results are shown in Table 1.

First, in an environment at a room temperature of 20° C. and a humidity of 50% RH, an oxygen barrier bag of a warming device to be measured and sealed in the oxygen barrier bag was opened, and one heat generating element stored in a bag was taken out of the warming device.

Separately, the temperature sensor of a data acquisition thermometer (LT-8, manufactured by Gram) was attached to an upper eyelid of a wearer and was fixed with a surgical tape. A warming device was then attached such that the topsheet 5 was in contact with the temperature sensor.

While a measuring instrument of the thermometer was connected to the temperature sensor, and the temperature was measured with time. Temperatures were measured at intervals of 10 seconds for about 60 minutes from the starting point of heat generation as the measurement starting point.

From a heat generation profile in which the vertical axis was measured temperature (° C.), and the horizontal axis was measurement time (sec), the time period when a temperature of 38° C. or more was recorded was regarded as a holding time at 38° C. or more. The maximum temperature in the temperature profile was regarded as a maximum temperature achieved.

[Evaluation of Water Vapor Generation Amount]

The total vapor amount of water vapor for 10 minutes from each warming device in Examples and Comparative Example was determined by the above method. A larger total vapor amount of water vapor for 10 minutes indicates that a warming device has better heat generation properties, generates a larger amount of water vapor, and can allow a heating object to sense both comfortable warm feeling and moisture. The results are shown in Table 1.

TABLE 1

| | | | Ex. 1 | Ex. 2 | Ex. 3 | Ex. 4 | Ex. 5 | Ex. 6 | Ex. 7 | Ex. 8 | Ex. 9 | Ex. 10 | Comp. Ex. 1 |
|---|---|---|---|---|---|---|---|---|---|---|---|---|---|
| Topsheet production method | | | Air-through | Air-through | Air-through | Air-through | Air-through | Air-through | Air-through | Air-through | Needle punching | Air-through | Needle pun-ching |
| Top-sheet struc-ture | First fiber layer | Resin composition of first fibers (core/sheath) | PET/PE | Only PET | Only PET | Only PET | Only PET | Only PET | PET/PE | PET/PE | Only PET | Only PET | PP/PE |

TABLE 1-continued

| | | Ex. 1 | Ex. 2 | Ex. 3 | Ex. 4 | Ex. 5 | Ex. 6 | Ex. 7 | Ex. 8 | Ex. 9 | Ex. 10 | Comp. Ex. 1 |
|---|---|---|---|---|---|---|---|---|---|---|---|---|
| | Fiber diameter of first fibers [μm] | 22 | 27 | 27 | 27 | 27 | 27 | 22 | 40 | 19 | 27 | 22 |
| | Basis weight of first fiber web [g/m²] | 40 | 12 | 12 | 20 | 20 | 20 | 60 | 20 | 80 | 20 | 24 |
| | Content of first fibers [% by mass] | 100 | 30 | 30 | 50 | 50 | 50 | 100 | 50 | 100 | 60 | 30 |
| | Resin composition of third fibers (core/sheath) | — | PP/PE | PET/PE | PET/PE | PET/PE | PET/PE | — | PP/PE | — | PP/PE | Only PP |
| | Fiber diameter of third fibers [μm] | — | 22 | 22 | 22 | 22 | 22 | — | 22 | — | 22 | 12 |
| | Basis weight of third fiber web [g/m²] | — | 28 | 28 | 20 | 20 | 20 | — | 20 | — | 20 | 56 |
| | Content of third fibers [% by mass] | — | 70 | 70 | 50 | 50 | 50 | — | 50 | — | 40 | 70 |
| | Number of fibers present in unit volume of first fiber layer [pieces/cm³] | 540 | 320 | 320 | 380 | 380 | 400 | 540 | 240 | 1300 | 330 | 1200 |
| Second fiber layer | Resin composition of second fibers (core/sheath) | PET/PE | PET/PE | PET/PE | PET/PE | PP/PE | PET/PE | — | PET/PE | — | PET/PE | — |
| | Fiber diameter of second fibers [μm] | 15 | 15 | 15 | 15 | 12 | 15 | — | 15 | — | 15 | — |
| | Basis weight of second fiber web [g/m²] | 20 | 20 | 20 | 20 | 20 | 20 | — | 20 | — | 20 | — |
| | Content of second fibers [% by mass] | 100 | 100 | 100 | 100 | 100 | 100 | — | 100 | — | 100 | — |
| | Number of fibers present in unit volume of second fiber layer [pieces/cm³] | 440 | 440 | 440 | 440 | 440 | 440 | — | 440 | — | 440 | — |
| Total basis weight [g/m²] | | 60 | 60 | 60 | 60 | 60 | 60 | 60 | 60 | 80 | 60 | 80 |
| Thickness of topsheet at starting point of heat generation T1 [mm] | | 2.4 | 3.5 | 3.8 | 4.5 | 4.7 | 4.5 | 2.6 | 3.6 | 1.8 | 4.8 | 1.4 |
| Thickness of topsheet 10 minutes after heat generation T2 [mm] | | 3.1 | 4.4 | 4.8 | 5.6 | 5.9 | 4.9 | 3.2 | 4.8 | 2.2 | 6.3 | 1.6 |
| Sheet thickness change amount (T2 − T1) [mm] | | 0.7 | 0.9 | 1.0 | 1.1 | 1.2 | 0.4 | 0.6 | 1.2 | 0.4 | 1.5 | 0.2 |
| Duration at 38° C. [min] | | 22 | 23 | 22 | 25 | 25 | 8 | 22 | 24 | 21 | 26 | 21 |
| Maximum temperature achieved [° C.] | | 40.0 | 40.0 | 40.0 | 40.0 | 40.0 | 39.0 | 40.0 | 40.0 | 40.0 | 40.0 | 40.0 |
| Water vapor generation amount [mg/10 min] | | 80 | 80 | 80 | 80 | 80 | 15 | 80 | 80 | 80 | 80 | 80 |
| Sensory evaluation | Topsheet smoothness [score] | 3 | 3 | 3 | 3 | 3.5 | 3 | 1 | 3 | 2.5 | 3.5 | 3 |
| | Topsheet softness [score] | 3.5 | 4 | 4.5 | 5 | 5 | 4.5 | 3.5 | 5 | 3 | 5 | 2 |
| | Warming device fitting properties [score] | 3 | 4 | 4 | 4.5 | 4.5 | 4 | 3.5 | 4.5 | 3.5 | 5 | 3 |
| | Productivity due to paper dust generation [score] | 2 | 2 | 2 | 1 | 1 | 1 | 2 | 3 | 3 | 5 | 3 |

As shown in Table 1, it is revealed that, in each warming device in Examples in which fibers containing a PET resin were used as the constituent fibers in the topsheet, the bulk of the topsheet was rapidly recovered immediately after use, and the warming device had softness, good touch feeling, and high fitting properties during use, as compared with the warming device in Comparative Example. In particular, using a heat generating element configured to generate water vapor at 10 mg or more/10 min has an advantage because heat is satisfactory applied.

This reveals that the warming device in the disclosure has good bulk recovery and has both excellent softness immediately after use and excellent fitting properties to the body of a wearer.

In the warming device in Example 8 as a preferred embodiment in the disclosure, the smoothness and softness of the topsheet and the fitting properties of the warming device were as excellent as those in Examples 4 and 5, but generation of paper dust was reduced. The reason for this is probably as follows: the first fibers used in Example 8 contained the PE resin having a lower melting point than the PET resin; accordingly, heat by air-through processing or the like fused the PE resin to form more fused points between constituent fibers; and consequently, constituent fibers including the first fibers were effectively prevented from falling or peeling off.

A reduction of paper dust generation prevents quality deterioration of materials due to generation or adhesion of paper dust during production of a warming device, and this can reduce the amount of unintended material wastes not satisfying the quality required in production. As a result, the warming device of the present invention is designed to reduce production costs and to improve productivity in the production and advantageously achieves a reduction in environmental load due to a reduction of wastes. The warming device further has an advantage in reducing contamination of a production apparatus or a production environment due to generation or adhesion of paper dust and in reducing accompanying labor or costs required for maintenance or cleaning.

Moreover, in the warming device in Example 10 as a more preferred embodiment in the disclosure, the softness of the topsheet was as excellent as that in Example 8, and the smoothness of the topsheet, the fitting properties of the warming device, and the productivity due to paper dust generation were especially excellent. The reason for this is probably as follows: the first fibers used in Example 8 contained a PET resin and a PE resin, but the first fibers used in Example 10 contained only a PET resin; accordingly, the bulk of the topsheet was easily recovered when the compressed state of the warming device was released; and an appropriate thickness was sufficiently maintained.

INDUSTRIAL APPLICABILITY

According to the present invention, a warming device having good bulk recovery after opening and having high fitting properties and feeling of use immediately after use is provided.

The invention claimed is:

1. A warming device, comprising:

a topsheet configured to be located close to a skin of a user;

a backsheet configured to be located far from the skin of the user; and a heat generating element interposed between the topsheet and the backsheet, wherein the heat generating element comprises an oxidizable metal, a carbon material, an electrolyte, and water, the heat generating element is configured to generate vapor from the heat generating element itself as heat is generated, the topsheet is a breathable fiber sheet including fibers comprising at least a polyethylene terephthalate resin, the topsheet has a multiple layer structure comprising a first fiber layer and a second fiber layer, the first fiber layer is provided at a side far from a skin of a user when the warming device is used, the second fiber layer is configured to contact the skin of a user when the warming device is used, the first fiber layer comprises first fibers and third fibers, the first fiber layer is the only fiber layer that comprises the first fibers, and the first fibers have a fiber diameter of more than 15 μm in plan view as measured by observation under a scanning electron microscope, and the second fiber layer comprises second fibers having a fiber diameter different than the first fibers.

2. The warming device according to claim 1, wherein the second fibers have a fiber diameter of 6 μm or more and 30 μm or less, and this fiber diameter is smaller than the fiber diameter of the first fibers.

3. The warming device according to claim 2, wherein the third fibers have a smaller fiber diameter than the fiber diameter of the first fibers, and have a larger fiber diameter than the fiber diameter of the second fibers.

4. The warming device according to claim 1, wherein the first fibers comprise the polyethylene terephthalate resin and a polyethylene resin.

5. The warming device according to claim 1, wherein the first fibers comprise the polyethylene terephthalate resin, and have a fiber diameter of more than 15 μm and 60 μm or less.

6. The warming device according to claim 2, wherein the second fibers comprise a polyethylene resin.

7. The warming device according to claim 3, wherein the third fibers comprise a thermoplastic resin other than a polyethylene phthalate resin.

8. The warming device according to claim 1, wherein a number of fibers present in a unit volume of the second fiber layer is 200 pieces/$cm^2$ or more and 1,500 pieces/$cm^2$ or less.

9. The warming device according to claim 1, wherein the topsheet is a fiber sheet in a sheet form that is maintained by at least one of fusion and entanglement of constituent fibers, and the topsheet has a contact part at which the constituent fibers are in contact with each other.

10. The warming device according to claim 1, wherein the topsheet has a thickness of 1.8 mm or more and 6.0 mm or less at a starting point of heat generation of the warming device.

11. A method for producing the warming device according to claim 1, comprising:

producing the topsheet, wherein in the producing the topsheet a laminate of a web of fibers containing a polyethylene terephthalate resin and a web containing fibers other than the web of fibers containing a polyethylene terephthalate resin is subjected to air-through processing.

12. A method for applying heat with the warming device according to claim 1, comprising:

bringing the topsheet into contact with an eye of a human so as to cover the eye; and providing heat to the eye and around the eye.

* * * * *